US008628948B2

(12) United States Patent
Yancey, Jr.

(10) Patent No.: US 8,628,948 B2
(45) Date of Patent: Jan. 14, 2014

(54) SYSTEMS AND METHODS FOR CULTIVATING, HARVESTING AND PROCESSING BIOMASS

(75) Inventor: Dennis Dwayne Yancey, Jr., San Jose, CA (US)

(73) Assignee: Coastal Waters Biotechnology Group LLC, San Jose, CA (US)

( * ) Notice: Subject to any disclaimer, the term of this patent is extended or adjusted under 35 U.S.C. 154(b) by 0 days.

(21) Appl. No.: 13/375,220

(22) PCT Filed: Jun. 2, 2010

(86) PCT No.: PCT/US2010/037037
§ 371 (c)(1),
(2), (4) Date: Feb. 16, 2012

(87) PCT Pub. No.: WO2010/141559
PCT Pub. Date: Dec. 9, 2010

(65) Prior Publication Data
US 2012/0202274 A1    Aug. 9, 2012

Related U.S. Application Data

(60) Provisional application No. 61/183,447, filed on Jun. 2, 2009, provisional application No. 61/263,340, filed on Nov. 20, 2009.

(51) Int. Cl.
*C12N 1/12* (2006.01)

(52) U.S. Cl.
USPC ...................................................... 435/257.1

(58) Field of Classification Search
None
See application file for complete search history.

(56) References Cited

U.S. PATENT DOCUMENTS

| | | | | |
|---|---|---|---|---|
| 4,416,993 | A * | 11/1983 | McKeown | 435/243 |
| 4,425,101 | A | 1/1984 | Krude | |
| 5,589,065 | A | 12/1996 | Bogatin et al. | |
| 6,030,535 | A | 2/2000 | Hayashi et al. | |
| 6,670,169 | B1 | 12/2003 | Schob et al. | |
| 6,768,109 | B1 | 7/2004 | Brokaw et al. | |
| 7,033,478 | B2 | 4/2006 | Harde | |
| 2004/0007452 | A1 | 1/2004 | Warren | |
| 2005/0029174 | A1 | 2/2005 | Collins | |
| 2005/0054101 | A1 * | 3/2005 | Felder et al. | 435/383 |
| 2009/0035856 | A1 | 2/2009 | Galliher et al. | |
| 2009/0130704 | A1 | 5/2009 | Gyure | |
| 2010/0102004 | A1 | 4/2010 | Holland | |
| 2011/0281340 | A1 | 11/2011 | Turner et al. | |

FOREIGN PATENT DOCUMENTS

| | | |
|---|---|---|
| WO | WO 00/75275 A2 | 12/2000 |
| WO | WO 00/75275 A3 | 7/2001 |
| WO | WO 2010/141559 A2 | 12/2010 |
| WO | WO 2010/141559 A3 | 4/2011 |

OTHER PUBLICATIONS

Ballester, et al. Process of desalination of low energy consumption and high compatibility with the use of renewable energies. International conference on renewable energies and power qualities(ICREPQ'09). Valencia, Spain. Apr. 15-17, 2009.

Penas, et al. Process of desalination of low energy consumption Magnetohydrodynamics desalination process. 2008.

Schafer. Laboratory research on desalination in a magnetic field using permselective membranes. Desalination. 1967; 3(2)174-182.

Takeda, etal. Flow control of seawater with a diverging duct by MHD separation method. IEEE transactions on applied superconductivity. 2004; 14(2):1543-1546.

International search report and written opinion dated Feb. 25, 2013 for PCT Application No. US2012/041766.

* cited by examiner

*Primary Examiner* — Suzanne M Noakes
*Assistant Examiner* — Stephen Chong
(74) *Attorney, Agent, or Firm* — Wilson Sonsini Goodrich & Rosati

(57) ABSTRACT

Combining controlled open-ocean iron enrichment with a system for collecting the ensuing biological growth can lead to a fundamental shift towards using marine biomass feedstock for large-scale global biodiesel production. The literature review reveals that open-ocean enrichment effectively reduces both the atmospheric carbon dioxide partial pressure and ocean acidity. A semi-closed ocean system is provided that allows for the efficient cultivation and harvesting of a high tonnage biomass feedstock generated by iron fertilization. The concept methodically capitalizes on the ocean's free nutrients, kinetic/potential energy, and expansive surface area to ensure that the mass, energy, and cost balance equations favor our system while taking care to preserve the ocean's ecosystem. The system is modular, portable, easily scalable system, and minimizes waste. In addition to the above benefits, our concept allows continued adherence to the NEPA and London Protocol by culling the biomass produced by fixing carbon dioxide and limiting iron exposure to the vessel's interior.

19 Claims, 7 Drawing Sheets

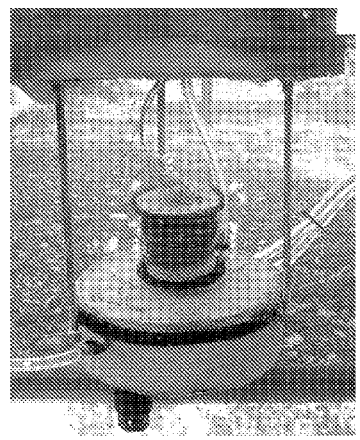
FIG. 9
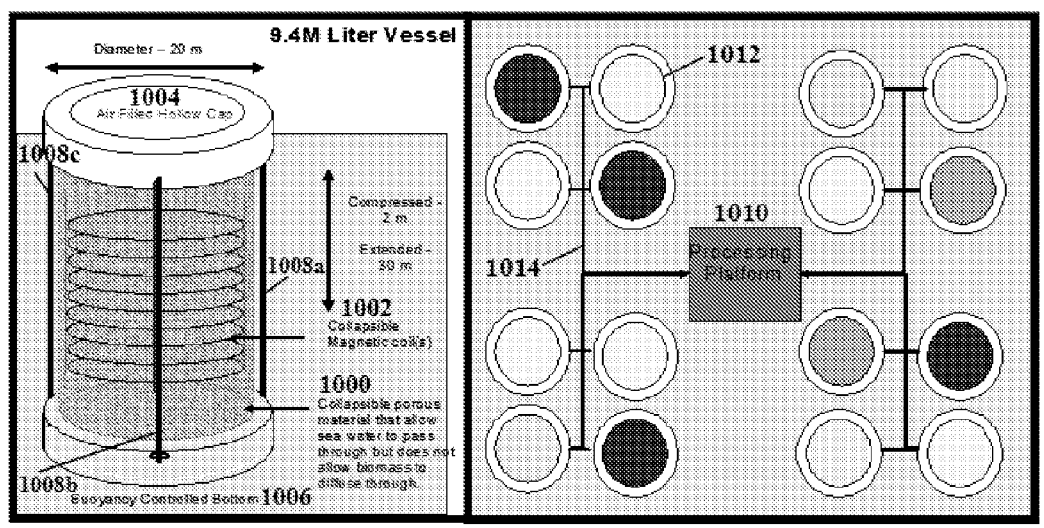
FIG. 10A
FIG. 10B

| Assumptions | | | |
|---|---|---|---|
| Initial Plankton Concentration (Pi) = | 0.0001 g/L | Biodiesel Density= | 0.88 g/mL |
| Specific Growth Rate (mu) = | 0.5 per Day | Lipid Content= | 30% |
| Vessel Expanded Volume = | 9,400,000 L | | |

| 5 million gallons per year biodiesel | | | |
|---|---|---|---|
| Daily | 326 Barrels | 51,889 Liters | 13,699 gallons |
| yearly | 119,139 Barrels | 18,939,394 Liters | 5,000,000 gallons |

| Plankton (Pi) (g/L) | Time (Days) | L Biodiesel/Vessel/Day | Vessels Required | Ocean Surface Area (Acres) |
|---|---|---|---|---|
| 100 | 27.6 | 11597.6 | 4 | 0.35 |
| 50 | 26.2 | 6105.1 | 8 | 0.66 |
| 25 | 24.9 | 3222.8 | 15 | 1.25 |
| 10 | 23.0 | 1391.7 | 37 | 2.89 |
| 1 | 18.4 | 174.0 | 296 | 23.13 |
| 0.1 | 13.8 | 23.2 | 2237 | 173.50 |

$$\Delta T \text{ (Day}^{-1}) = \frac{\ln[P_f/P_i]}{\mu} \quad \text{Eq. 1}$$

$$\frac{\text{Biomass(g)}}{\text{Day * Vessel}} = \frac{P_f * \text{Volume per vessel}}{\Delta T} \quad \text{Eq. 2}$$

$$\frac{\text{Lipids (g)}}{\text{Day * Vessel}} = \frac{\text{Biomass(g)}}{\text{Day * Vessel}} \times 20\% \text{ (max. lipid content)} \quad \text{Eq. 3}$$

$$\frac{\text{Biodiesel (L)}}{\text{Day * Vessel}} = \frac{\text{Lipid (g)}}{\text{Day * Vessel}} \times \frac{\text{Biodiesel(g)}}{\text{Lipid (g)}} \times \frac{1}{880 \text{ g L}^{-1}} \quad \text{Eq. 4}$$

$$\text{\# of Vessels} = \text{US Daily Distillate Consumption} \div \frac{\text{Biodiesel (L)}}{\text{Day * Vessel}} \quad \text{Eq. 5}$$

$$\text{Vessel Area (m}^2) = \mu * r^2 \quad \text{Eq. 6}$$

FIG. 13

| Assumptions | | | |
|---|---|---|---|
| Initial Plankton Concentration (Pi) = | 0.0001 g/L | Biodiesel Density= | 0.88 g/mL |
| Specific Growth Rate (mu) = | 1.2 per Day | Maximum Lipid Content= | 20% |
| Vessel Expanded Volume = | 9,400,000 L | | |

| US Petroleum Distillate Consumption | | | |
|---|---|---|---|
| Daily | 4,300,000 Barrels | 688,000,000 Liters | |
| yearly | 1,569,500,000 Barrels | 251,120,000,000 Liters | |

| Plankton (Pf) (g/L) | Time (Days) | L Biodiesel/Vessel/Day | Vessels Required | Ocean Surface Area (Acres) |
|---|---|---|---|---|
| 100 | 11.5 | 18556.2 | 37,077 | 2,876 |
| 50 | 10.9 | 9768.2 | 70,433 | 5,463 |
| 25 | 10.4 | 5156.5 | 133,425 | 10,348 |
| 10 | 9.6 | 2226.7 | 308,971 | 23,963 |
| 1 | 7.7 | 278.3 | 2,471,768 | 191,705 |
| 0.1 | 5.8 | 37.1 | 18,538,260 | 1,437,790 |

FIG. 14

SYSTEMS AND METHODS FOR CULTIVATING, HARVESTING AND PROCESSING BIOMASS

CROSS-REFERENCE TO RELATED APPLICATION

This application is related to U.S. Provisional Application No. 61/183,447, filed Jun. 2, 2009, and U.S. Provisional Application No. 61/263,340, filed Nov. 20, 2009, which are hereby incorporated by reference in their entirety.

BACKGROUND OF THE INVENTION

Unfortunately, the United States' economy and lifestyle are based on having a steady and inexpensive petroleum hydrocarbon supply available for import from foreign sources. Consequently, this petroleum supply and demand dynamic will siphon more and more hard capital and jobs from the domestic economy as the century progresses due to diminishing crude oil reserves. Earth's crude oil reserves are large but finite in volume. Many scientists predict that crude oil production from proven reserves will peak within this century. The decline in production will adversely affect the United States' oil-based economy and lifestyle. Due to impending fossil fuel supply issues this century, the U.S. continues to shift significant resources to identify realistic and economically viable avenues to produce a domestic renewable hydrocarbon equivalent.

Initially, U.S. scientists focused on using fatty acids from terrestrial plants and animals to make biodiesel fuels. The biodiesel produced is a compatible substitute for fossil fuel diesel but not close to being a robust inexpensive equivalent. The main issues with using terrestrial plant and animal fatty acids are:
- These feedstocks are expensive and account for as much as 80% of the fuel's cost. According to Anthony Radich and Rudy Pruszko, the best way to reduce renewable diesel and jet fuel production cost is by lowering feedstock cost. See, e.g., Pruszko, R (2007), "Alternative Feedstocks and Biodiesel Production", Presented at the Practical Biodiesel Blueprint Conference, Radich, A. (2004); "Biodiesel Performance, Costs, and Use" Energy Information Administration, p 4, Website http://www.eia.doe.gov/oiaf/analysispaper/biodiesel/pdf/biodiesel.pdf, which is hereby incorporated by reference in its entirety.
- There are limited quantities of tallow, waste vegetable oil (WVO), and soybeans.
- Terrestrial feedstocks cultivation compete with other needs for land and water resources.
- Several plant feedstocks are also foods thus increasing the demand on a limited supply.

In order to address these issues, renewable fuel research has focused on microalgae cultivated in freshwater ponds and bioreactors because of their high yield per hectare as well as their high lipid and protein composition relative to other photoautotrophs. See, e.g., Ingole B S, Parulekar A H, (1995) "Biochemical-Composition Of Antartic Zooplankton From The Indian-Ocean Sector" Indian Journal Of Marine Sciences 24(2): 73-76, which is hereby incorporated by reference in its entirety. The problems with using microalgae produced from land based aquacultures, ponds, and bioreactors are: high capital cost, high fresh water consumption, generates waste streams, not portable, and not easily scalable.

Therefore, a need exists for improved systems and methods for cultivating biomass. A further need exists for improved systems and methods for harvesting and processing biomass.

SUMMARY OF THE INVENTION

The invention provides for terrestrial microalgae aquacultures and bioreactors that can be used to cultivate microalgae in open water environments to generate a steady and inexpensive feedstock. The systems, devices, and methods described herein can be used to produce renewable fuels, natural and engineered proteins, and for bioremediation.

The invention provides for improved growth and production of biomass in a vessel situated in open-water environment by retaining iron and iron compounds within the vessel.

The vessels can include semi-permeable membranes, magnetic fields, buoyancy controlled components, and/or baffles that allow for efficient and cost-effective growth and production of biomass. The vessels can be designed to withstand harsh environmental conditions, while allowing exchange of nutrients through the semi-permeable walls of the vessel.

In accordance with an aspect of the invention, a vessel can comprise a semi-permeable exterior wall, wherein the semi-permeable exterior wall selectively retains a microorganism over water-soluble nutrients; and a baffle for directing flow within the vessel in a recirculating pattern when fluid is passed through the vessel.

In accordance with another aspect of the invention, a vessel may comprise a buoyant top; a buoyancy-controlled base; and a semi-permeable mesh material connecting the buoyant top to the buoyancy-controlled base, wherein the semi-permeable mesh material selectively retains a microorganism over water-soluble nutrients.

A system for producing biomass may be provided in accordance with another aspect of the invention. The system may include a vessel in an aquatic environment capable of growing a microorganism in an interior region enclosed therein, wherein the vessel has a semi-permeable material capable of retaining the microorganism in the interior region while allowing fluid from the aquatic environment to flow through. The system may also include a processing platform in fluid communication with the interior region of the vessel and configured to harvest the microorganism from the vessel.

One or more vessels can be secured to existing open-water structures, such as oil-well platforms, barges and boats, and shoreline. A mobile or fixed processing platform can be connected to the vessels to allow for processing of the biomass products.

An aspect of the invention provides a method for producing biomass. The method for producing biomass can include growing a microorganism in a vessel comprising a semi-permeable membrane in an aquatic environment; and retaining iron compounds within the vessel.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

A better understanding of many of the features and advantages of the invention will be obtained by reference to the following detailed description that sets forth illustrative embodiments, in which many of the principles of the invention are utilized, and the accompanying drawings of which:

FIG. 9 shows a vessel base with an electromagnetic solenoid for producing a magnetic field and fluidic connections for providing a stream of carbon dioxide.

FIG. 10A shows a vessel for plankton cultivation having a collapsible magnetic coil.

FIG. 10B shows top view of a biomass processing system having a plurality of vessels connected to a processing platform that allows for farming of open water, e.g., the ocean.

FIG. 13 shows equations relating to the scaling of biomass production.

FIG. 14 shows a table showing system scaling based on final vessel plankton concentration and the US daily petroleum distillate consumption.

DETAILED DESCRIPTION OF THE INVENTION

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention provides systems and methods for cultivating, harvesting, and processing biomass. Various aspects of the invention described herein may be applied to any of the particular applications set forth below or for any other types of feedstock. The invention may be applied as a standalone system or method, or as part of a biofuel or biomass production system or method. It shall be understood that different aspects of the invention can be appreciated individually, collectively, or in combination with each other.

The invention provides for various designs, methods, and systems that allow for the goals set forth herein for the growth of one or more microbial organism and the various beneficial effects of the growth, including the production of a renewable fuel, remediation, and production of proteins. The invention provides for design features that will improve the specific growth rates, product density/specificity, and prevent trace metals from being diluted by ocean or open-water currents. These features and combinations of these features have not been incorporated in prior ocean enclosure systems. See, e.g., Brockmann U H, Dahl E, Kuiper J, et al. (1983). "The Concept Of Poser (Plankton Observation With Simultaneous Enclosures In Rosfjorden)" Marine Ecology-Progress Series 14 (1): 1-8; S. Takeda, J. N., C. S. Wong, F. A. Whitney, W. K. Johnson, and T. J. Soutar. (1999). "Application of open-ocean enclosures to study the control of biological carbon dioxide pump in the subarctic North Pacific Ocean." Proceedings of the 2nd International Symposium Carbon Dioxide in the Oceans: 583-586; and Wang, J. K. (2003). "Conceptual Design of a Microalgae-based recirculating oyster and shrimp system. Aquacultural Engineering 28: 37-46, which are hereby incorporated by reference in their entirety.

Figure 1:
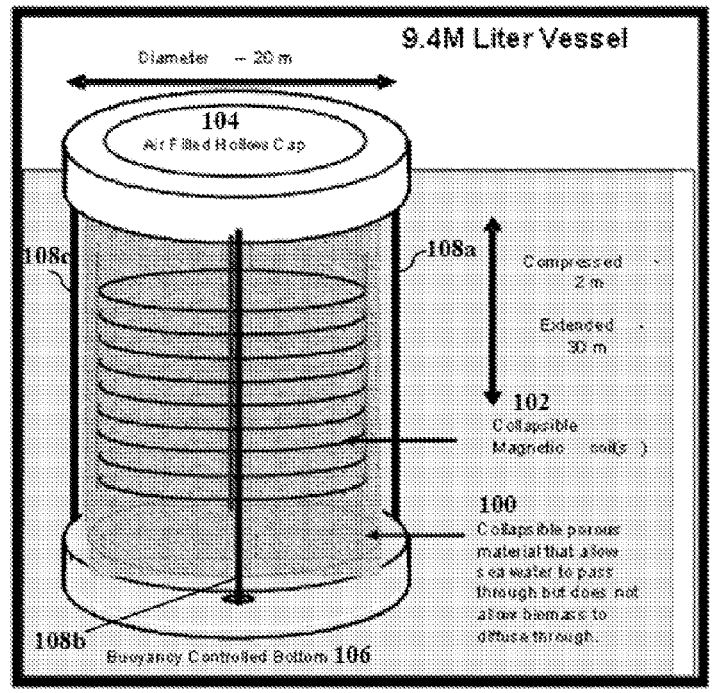
FIG. 1 shows a vessel design that incorporates a magnetic core to retain ferromagnetic iron sulfate and a porous material exterior to (a) retain the oxidized iron, other trace metals, and the induced microalgae and (b) allow hydrophilic micronutrients to enter the vessel.

FIG. 1 shows an example of an open-water enclosure in accordance with an embodiment of the invention. A collapsible porous material 100 may be provided that may allow sea water to pass through but does not allow biomass to diffuse through. The collapsible porous material may be mesh netting. Open-water enclosures can utilize mesh netting with small pore sizes. For example, mesh netting may utilize pore sizes less than 30 μm. Mesh of this size may allow continuous nutrient replenishment through the mixing by ocean currents, which captures the microalgae product. The mesh netting can be of any pore size and/or material that allows for selection against loss of trace metals and biomass while allowing transport of other nutrients. The selection may be charge, size, and/or hydophobicity/hydrophilicity based.

An open water enclosure may include a magnetic core 102. In some embodiments, the magnetic core may be a collapsible magnetic coil.

A large buoyant top 104 to support the structure can be incorporated. The top structure may or may not enclose the vessel. In some embodiments, the top structure may be an air filled hollow cap. In some embodiments, the structure may include a buoyancy controlled bottom 106. Optionally, the vessel may include one or more reinforcement beams 108a, 108b, 108c.

Open ocean/water cultivation can allow for following advantages:
  Free nutrients,
  Free kinetic energy for mixing,
  Free organism cooling and hydration,
  The ocean's vast surface area eliminates natural scaling limitations, and/or
  Portability and ease of implementation in most ocean environments.

As a result of these advantages, the products generated, including renewable fuels, can be produced for significantly less cost. A hydrocarbon equivalent can also be produced at a significantly lower cost by various processes, including hydrotreating an oil extract.

Hydrotreating oil extracts allows for the production of a renewable diesel that can:
  Be a biofuel indistinguishable from petroleum diesel,
  Be a drop-in replacement for or can be blended to any proportion with traditional diesel,
  Be used in any proportion in today's infrastructure from pipelines and storage to gas pumps and automobiles,
  Be used in any proportion,
  Has excellent stability and is not oxygenated,
  Offer superior cold flow properties making it more suitable for very cold climate conditions,
  Have higher energy content per volume compared to Biodiesel, and/or
  Offer lower fossil energy requirements and reduction of Green House Gases and NOx emissions.

Iron Fertilization

In some embodiments of the invention, vessels may be used to capture all or substantially all biological growth induced by iron fertilization, which can be accomplished by the exposure of the organism to trace metals that are confined within the vessel. Metals within the vessel may include reduced iron. In order to prevent the reduced iron from diffusing outside the vessel, the vessels may include an electromagnetic or permanent magnetic core designed to minimize reduced iron dilution by ocean currents or other currents. Other nonmagnetic metals and oxidized iron may be captured by a charged fiberglass material that may allow hydrophilic nutrients through but retain the microalgae and trace element. The material need not be made of fiberglass and can be formed from other materials that provide similar selection characteristics.

Microalgae may require iron to assist in converting carbon dioxide into sugars using light energy from the sun. The oceans iron concentrations are generally well below the levels required to induce exponential growth in marine algae. As a result, marine microalgae are by and large in a stationary phase until storms or other natural events transport iron from land sources to coastal waters. Trace metals, especially iron, are high beneficial for inducing microalgae growth in ocean environments. See, e.g., Martin J H, Coale K H, et al (1994), "Testing The Iron Hypothesis In Ecosystems Of The Equatorial Pacific-Ocean" Nature 371 (6493): 123-129; Coale, K H, and et al. (1996). "A massive phytoplankton bloom induced by an ecosystem-scale iron fertilization experiment in the equatorial Pacific Ocean." Nature 383: 495-501; Zhou G J, Bi Y H, Zhao X M, et al. (2009) "Algal Growth Potential And Nutrient Limitation In Spring In Three-Gorges Reservoir, China" Fresenius Environmental Bulletin 18(9): 1642-1647; Marchetti A, Varela D E, Lance V P, et al. (2010) "Iron and silicic acid effects on phytoplankton productivity, diversity, and chemical composition in the central equatorial Pacific Ocean" Limnology and Oceanography 55(1):11-29; Coale, K H (1991). "Effects of iron, manganese, copper, and zinc enrichments on productivity and biomass in the subarctic Pacific" Limnology and Oceanography 36: 1851-1864; and Coale K H, Johnson K S, Chavez F P, et al. (2004). "Southern Ocean Iron Enrichment Experiment: Carbon Cycling in High- and Low-Si Waters." Science 304(5669): 408-414 (herein after the "2004 Coale paper"), which are hereby incorporated by reference in their entirety. Artificially elevating iron concentrations in the open ocean is one key to inducing marine microalgae growth as a feedstock for industrial scale renewable diesel and jet fuel production.

In the 2004 Coale paper, microalgae growth was induced by adding iron sulfate to 0.7 nM in a 225 $km^2$ area in the arctic polar front zone of the southern seas. The microalgae eventually covered approximate 2400 $km^2$ after 20 days of growth. Assuming the microalgae had at least a depth of 10 m and a density of at least 1 µg/L, this can yield a wet microalgae biomass of approximately 26.5 tons. In some embodiments, algae growth can be tailored toward biological sequestration of carbon dioxide. In other embodiments, algae growth can be tailored toward the production of a renewable fuel feedstock.

In order to control the cultivation and harvesting of the microalgae induced by iron fertilization, several vessels can be utilized with the following design goals:
  To contain microalgae and iron while allowing hydrophilic nutrients to pass between the vessel and the surrounding environment.
  To concentrate microalgae 15× prior to harvesting in order to reduce the volume of seawater to be processed and discarded and in turn to reduce the energy requirements to process the microalgae.

In some embodiments, the goal can be to capture all biological growth induced by iron fertilization, which can be accomplished by allowing the organism to be exposed to the trace metals only in the confines of the vessel.

Vessel Design

A semi-closed plankton cultivation and processing system, including a vessel, is shown in FIG. 1 and FIG. 10A. The system can include a control system (not shown) for analyzing and processing, among other things, environmental conditions, nutrient parameters and vessel status. This vessel has several innovations that improve the specific growth rates, product density/specificity, contain (or capture) organisms to be grown, and prevent trace metals from being diluted by ocean currents.

In some embodiments, the vessel may have a substantially cylindrical shape. For example, a cross-sectional area of the vessel may have a circular shape. In other embodiments, the vessel may have any other shape, which may include a prism with a square cross sectional shape, diamond cross-sectional shape, rectangular cross-sectional shape, triangular cross-sectional shape, pentagonal cross-sectional shape, hexagonal cross-sectional shape, octagonal cross-sectional shape, or elliptical cross-sectional shape. In some embodiments, the vessel cross-sectional shape may correspond to a shape of a top apparatus and/or bottom base.

The vessel may include a collapsible porous material 100 that may allow sea or ocean water to pass through without allowing biomass to diffuse through. In some embodiments, the collapsible porous material may be a mesh netting. The collapsible porous material may be formed from a fabric or textile, such as a cotton canvas material. In some embodiments, the porous material may be formed of a synthetic, non-synthetic, or blended fiber. The porous material may be formed of one or more materials. The porous material may be a filtration membrane. The porous material may be flexible enough to allow stirring by ocean currents. In some embodiments, the porous material may be porous enough to allow sea/ocean/surrounding water to diffuse through. The material may also be dense enough to contain product within the vessel, by making its diffusion timescale sufficiently large. Various embodiments of the porous material are discussed further below.

The collapsible porous material may surround a magnetic core 102. In some embodiments, the magnetic core may be one or more collapsible magnetic coil. The magnetic core may include any magnetic material. Preferably, the magnetic material may have a shape or configuration that may enable it to collapse in a vertical direction. For example, it may include a coil, telescoping features, sliding features, folding features, accordion-type features, small loose components, or other configurations that enable collapsing. Various embodiments of the magnetic core are discussed further below.

The collapsible porous material may be provided between a top apparatus 104 and a bottom base 106 of the vessel. One or more reinforcing beams 108a, 108b, 108c may be provided between the top apparatus and the bottom base.

The exterior vessel design incorporates innovative ideas to reduce energy consumption and operating cost requirements. One feature is a buoyant top apparatus to support the structure. In some embodiments, the top apparatus may be filed with air. In other embodiments, the top may be filled with another gas or material that may have less density than water. In some embodiments, the top may be hollow or may include pores that may trap air or other gases. The top apparatus may be formed of any material or have any configuration that may allow the top apparatus to float on the ocean's surface.

Figures 2A, 2B:
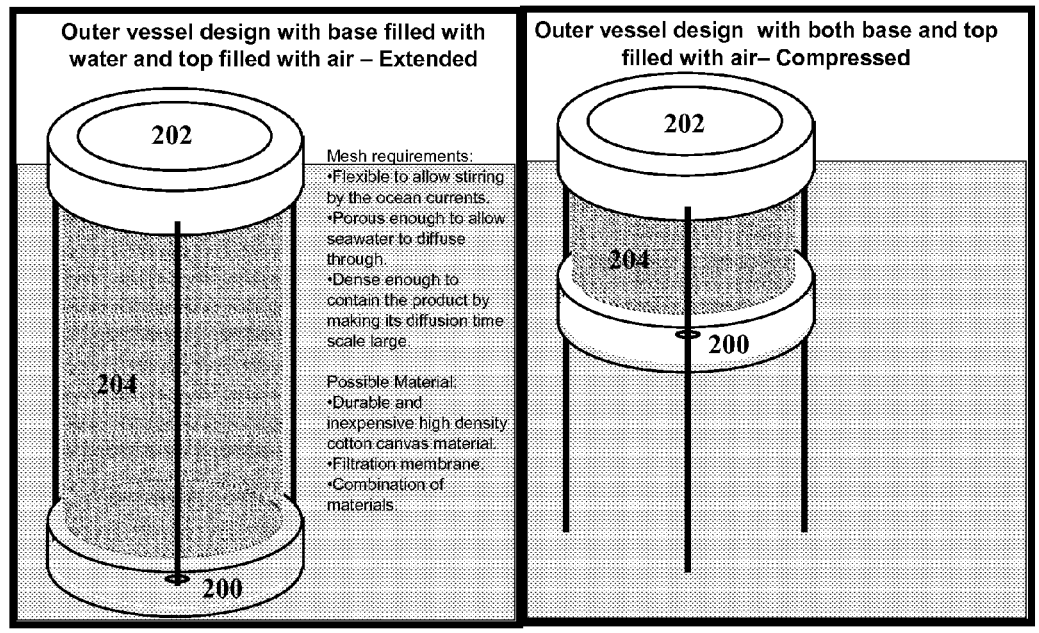
FIG. 2A shows a vessel with a compression mechanism, which permits bioreactor volume reduction in an extended state.
FIG. 2B shows the vessel shown in FIG. 2A in a compressed state.

The concept significantly improves the functionality of the vessel by adding a buoyancy controlled base as shown in FIG. 1 and FIG. 10A. FIG. 2A shows that when the base 200 is filled with water, it expands the cultivation volume/depth of the vessel. In some embodiments, the vessel may be expanded so that the base reaches of a depth of 30 m. In other embodiments, when the vessel is expanded, the base may be at any depth, which may include but is not limited to about, up to about, or greater than about 100 m, 70 m, 50 m, 40 m, 35 m, 30 m, 25 m, 20 m, 15 m, 10 m, 7 m, or 5 m.

Once the biomass has reached a predetermined density, air is pumped into the base 200 causing the cultivation volume/ depth to decrease as the base rises. The base may be brought closer to a top 202 of the vessel. As the vessel approaches the compressed state in FIG. 2B, the product concentration increases by as much as 15×. In some embodiments, the concentration can increase about, up to about, or greater than about 5, 10, 15, 20, 25, 30×. Concentration can be achieved by flow or efflux of water, such as seawater, through a semi-permeable meshing 204. This critical processing step significantly reduces the volume of seawater and in turn reduces the energy requirements for the pumps and dewatering centrifuges during biomass processing.

Semi-Permeable Meshing

A variety of materials may be chosen for the flexible porous material that allows seawater to pass freely but impedes plankton (or other biomass or fuel) diffusion out of the vessel. In some embodiments, the vessel includes a porous material that may be constructed of Nitex netting with a pore size less than 20 $\|$m, a fiberglass upper portion, and a lower buoyancy control base. The netting can be protected from rips by something similar to a high density cotton canvas exterior. Polyamine and polyethylene netting material with pores less than 20 μm can be used. Other materials can also be used. One, two, three, four, or more layers of flexible porous material may be provided. In some embodiments, the layers may be formed of the same material, while in other embodiments, the layers may be formed of different materials. In some instances, the layers may have the same pore size, while in other instances, the layers may have different pore sizes.

Functionally, the mesh may allow for transport of water and other small molecules through the mesh and retention of organisms to be grown, such as those described herein. The mesh may be a semi-permeable exterior wall that selectively retains the organisms over water-soluble nutrients. For example, the wall can retain more organisms than water-soluble nutrients. For example, the wall can retain 2×, 3×, 5×, 10×, 15×, 20×, 30×, 40×, 50×, 70×, 100×, 200×, 500×, 1000× or more organisms than water-soluble nutrients by mass, concentration or volume. The prototype can be tested in a 3 million gallon closed water environment at Moss Landing Commercial Park (MLCP) for construction and material quality. A plankton concentration time course can be conducted by inoculating the vessel interior with plankton so that a initial vessel concentration of 1 g/L is achieved and measure for Chlorophyll a (Chl a) inside and outside the vessel.

Not only for efficiency concerns, but also for environmental concerns, the semi-permeable material can be selected to minimize the transport of biological mass to the surrounding environment. The correct combination of materials and construction can be achieved when the baseline Chl a levels in the seawater are maintained outside the vessel while maintaining close to the original 1 g/L plankton concentration inside the vessel.

Magnetic Core Design

Trace metals, especially iron, are the key to inducing plankton growth in ocean environments. Since the goal is to capture all biological growth induced by iron fertilization, it may be desirable for organism exposure to the trace metals to occur only in the confines of the vessel. In order to prevent the trace metals from diffusing outside the vessel, an electromagnetic core designed to minimize trace metal dilution by ocean currents is provided. Para- and ferromagnetic particles may be retained within the vessel.

Figures 11, 12A, 12B:
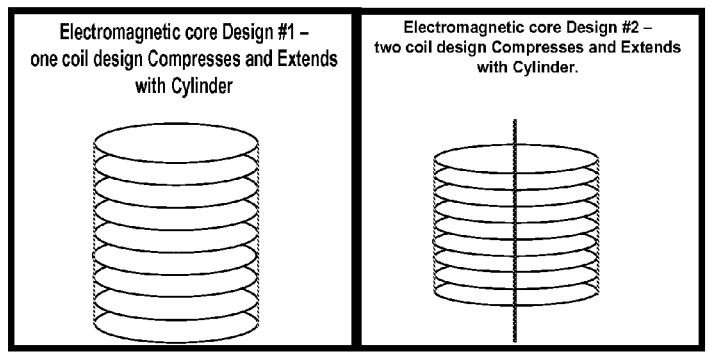
FIG. 11 shows a table with calculations for determining the number of vessels required to produce 5 million gallons per year at various final concentrations of microalgae.
FIG. 12A shows an electromagnetic core design having a single electromagnet that can produce a constant and large enough electromagnetic field to ensure that trace metals remain in the vessel that can compress and extend with the vessel.
FIG. 12B shows an electromagnetic core having a first electromagnet positioned at the perimeter of the vessel and a second electromagnet positioned at the center of the vessel to promote mixing and/or movement of trace metals between the electromagnets.

Examples of potential electromagnetic cores are depicted FIG. 12A and FIG. 12B. The one electromagnetic field in FIG. 12A is constant and large enough to insure that the trace metals, especially iron, remain in the vessel. A one-coil design may include a magnetic coil that may compress and extend with a vessel. It may be possible to tailor trace metal concentrations to the prevailing organism growth conditions by varying the electromagnetic field intensity as a form of controlled release. An alternative is the design in FIG. 12B that incorporates an electromagnetic field at the perimeter and in the center of the vessel. A two-coil design may be provided, which may compress and extend with the vessel. Alternating the electromagnetic field between the two electromagnets promotes trace metal mixing within the vessel while preventing them from being diluted.

One or more electromagnetic coils may be in electrical communication with a power source. The power source may be part of the vessel or may be external to the vessel.

As previously described, a magnetic core may include a magnet or electromagnet that may be compressible or collapsible. The magnetic core can preferably be compressible or collapsible in a vertical direction.

The magnetic core may be enclosed by the vessel. For example, the magnetic core may be enclosed by a semi-permeable or porous material. The magnetic core may be entirely closed by the semi-permeable or porous material. In some embodiments, the magnetic core may be at least partially enclosed by the semi-permeable or porous material.

Exemplary Vessel Designs

One embodiment of a vessel is shown in FIG. 1 and FIGS. 2A and 2B. A vessel can have one or more of the following design features:

Variable and/or collapsible electromagnetic core to retain the reduced iron sulfate as shown in FIG. 1.

Constant replenishing of hydrophilic nutrients.

Constant dilution of waste organic acids excreted by the microalgae.

Culture never dehydrates or over heats.

Concentrates organism by reducing vessel volume as shown in FIG. 2.

The vessel, as shown in FIG. 1, may have a maximal volume of 9.4 million liters, a diameter of 20 meters, and a height that can be adjusted from 2 meters to 30 meters. The vessel may contain a compressible or collapsible magnetic or electromagnetic core 102 that can facilitate retention of trace metals, e.g., magnetic trace metals, or iron. The vessel may be cylindrical in shape or any other suitable shape. Any discussion herein of a cylindrical shape may apply to any other shape and vice versa.

The circumferential walls 100 of the vessel may be made of a mesh material that allows selective transport of nutrients, e.g., nitrogen, phosphorous, water, waste products, trace metals, and biomass. The mesh material may be made of fiberglass with a particular pore size. In some embodiments, the porous material may be made of a plastic, a metal, a glass, an organic material, or any combination thereof that has the desired selectivity. In some embodiments of the meshes or nettings, or porous materials described herein can be fabricated using fiberglass fabric, carbon fiber fabric, polyethylene, polyvinylacetate, or hydrophilic polymer. These materials can be woven. In some embodiments of the invention, these materials can be charged, e.g., fiberglass fabric. Some other examples of materials include, e.g., a durable and inexpensive high density cotton canvas material, a filtration membrane, a metallic sheet, any woven hydrophilic fabric or polymer (e.g., woven polypropylene, woven polyethylene), or membrane with a selected pore size. Selected pore sizes include any pore size of about or up to about 1, 5, 10, 15, 20, 25, 30, 40, 50, 75, 100, 150, 200, 250, 300, 500, 1000, 2000, 3000, or 5000 microns. In some embodiments, the pore size may be variable or uniform across the surface of the mesh material or into the mesh material. Alternatively, pore size may vary within the mesh material. The pores may be evenly distributed over the mesh material, may be grouped into clusters, or may have any other distribution over the mesh material.

As stated previously, the selectivity can be achieved by pore size, charge, hydrophilicity/hydrophobicity, magnetism, or any combination thereof. In some embodiments, the selectivity is obtained by providing for a material that has a relatively greater diffusion time for the biomass and other materials to be retained as compared to materials that are to be exchanged with the surrounding environment.

The top 104 of the vessel and the base 106 of the vessel can be connected in a variety of manners. In some embodiments, the top and base are connected only by the cylindrical walls 100 of the vessel. An interior region of the vessel may be enclosed by the cylindrical walls and/or the top and base. The cylindrical walls may or may not be flexible and/or collapsible. In some embodiments, the cylindrical walls are rigid. The top and base of the vessel can be movable with respect to one another. They may be movable in a vertical direction. They may or may not be movable in a horizontal direction. In one example, when organisms are contained within the vessel, the top and base of the vessel may be brought into closer proximity with one another. The top and base may be brought into closer proximity while the walls are collapsed. The walls may optionally be collapsed without expanding horizontally. In some embodiments, the walls may be collapsed while maintaining a substantially same cross-sectional area enclosed therein. This may reduce the volume within the vessel. Reducing the volume of the vessel may result in increasing concentration of the organism therein.

In other embodiments, the top and base are connected by the cylindrical walls and one or more reinforcing beams 108a, 108b, 108c. In some embodiments, one, two, three, four, five, six, seven, eight, or more reinforcing beams may be provided. The reinforcing beams can provide for a rigid connection between top and base, while the cylindrical walls can remain flexible. The one or more reinforcing beams can limit them mobility of the base with respect to the top. For example, the reinforcing beam can limit the mobility of the base with respect to the top in a vertical direction. The base may move along the rigid reinforcing beams (as shown in FIG. 2) and/or the rigid cylindrical walls such that the base moves vertically and is prevented from translating horizontally away from the top of the vessel. In some embodiments, the reinforcing beams may remain fixed with respect to the top of the vessel, and the base may slide with respect to the reinforcing beams. Alternatively, the reinforcing beams may be fixed with respect to the base of vessel, and the reinforcing beams may slide with respect to the top of the vessel. In other embodiments the reinforcing beams may be movable with respect to both the top and bottom of the vessel. In some embodiments, the top and/or bottom may include one or more vertical channel or passage that may be capable of sliding with respect to the reinforcing beam. In other embodiments, the top and/or bottom of the vessel may be provided between the reinforcing beams. The top and/or bottom of the vessel may be configured to remain at a substantially fixed horizontal/lateral position with respect to the reinforcing beams.

The position of the vessel base relative to the top of the vessel can be controlled in a variety of manners, e.g., buoyancy and/or mechanically controlled. In some embodiments, the base and the top of the vessel may be buoyancy controlled. The top of the vessel may be an air filled hollow cap and the base of the vessel may be negatively buoyant. The base may also have one or more compartments that allow for buoyancy control. In some embodiments, the compartments may be or may contain bladders that can hold air or another gas. Once the bladders are filled with gas, the base may become positively buoyant and cause the base to rise toward the top of the vessel. The bladders can be filled in a manner such that the rate of vessel volume reduction or expansion is controlled. This may be important to increase the selectivity of porous cylindrical walls, e.g., to selectively allow transport of water and other undesired materials across the porous walls and retain iron and biomass. The bladders may be in communication with one or more gas source. For example, one or more hose or channel may connect the bladders to a gas source. In some embodiments, a pump, or positive pressure source may be provided to force gas into the bladders to raise the base. The bladders may also be in communication with one or more gas vent, when it is desirable to lower the base. The bladders may vent directly to the surrounding water, or may be connected to a remote venting location via a hose or channel. In some embodiments, the remote venting location may be the same as, or different from, the gas source.

In some embodiments, a vessel base may be raised and/or lowered via one or more mechanical actuator. For example, the base and/or top may move relative to a reinforcing beam via an actuator. Examples of actuators may include but are not limited to, motors, solenoids, linear actuators, pneumatic actuators, hydraulic actuators, electric actuators, piezoelectric actuators, or magnets. Actuators may cause the base and/or reinforcing beam to move based on a signal received from a control system. The actuators may or may not be connected to a power source.

Figure 3A:
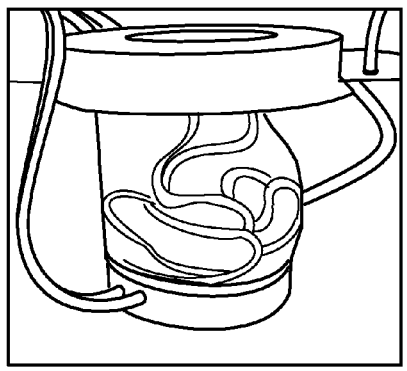
FIG. 3A shows a vessel having a fiberglass composite top and based with a fiberglass mesh material that allows nutrients to be exchanged, while retaining marine microalgae within.
Figure 3B:
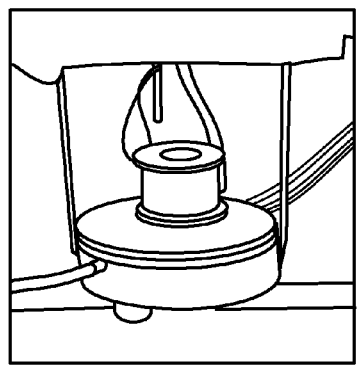
FIG. 3B shows an exposed electromagnetic solenoid and carbon dioxide bubbling from the fiberglass composite base.
Figure 3C:
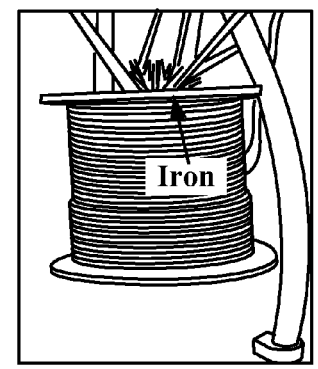
FIG. 3C shows iron powder applied to a solenoid that can provide an induced magnetic field to orient and retain iron within the vessel.
Figure 4A:
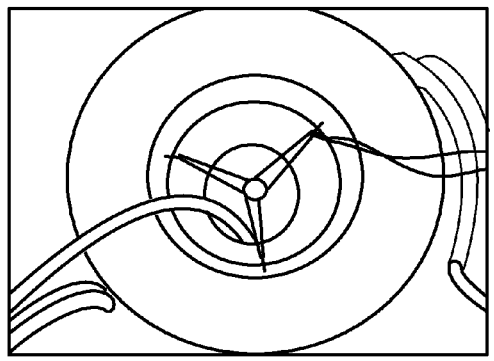
FIG. 4A shows a top view of a two-liter vessel with a fiberglass fabric exterior and a centrally located electromagnet.
Figure 4B:
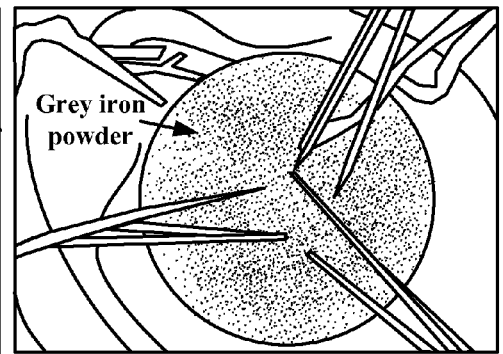
FIG. 4B shows a close-up top view of the two-liter vessel after three days.

FIGS. 3A, 3B, 3C, 4A, and 4B show an example of a vessel described herein. The electromagnetic vessel can be referred to as the Iron Fertilization Vessel (IFV). A $1^{st}$ generation 2 L prototype IFV (FIG. 3A) has been built and has successfully been shown to confine growth to IVF's interior (FIGS. 4A and 4B), to limit iron exposure to the IVF's interior by inducing an electromagnetic field (FIG. 3C), to concentrate the culture 3× prior to harvesting by compressing IFV's volume, and to blow carbon dioxide gas from the base (FIG. 3B). FIG. 4A shows the 2 L vessel prior to incubation in water (t=0). FIG. 4B shows the 2 L vessel after three days of incubation in water. The grey matter is the reduced iron powder attached to the magnet. Red matter on the walls of the fiberglass fabric is mostly oxidized iron retained by the fiberglass fabric. The oily substance present throughout the interior of the vessel shown in FIG. 4B may indicate the presence and/or growth of microalgae.

The $1^{st}$ generation IFV prototype is equipped with a two ply of an 8.5 oz 2×2 twill weave fiberglass mesh, a fiberglass composite top, and buoyancy controlled base, as shown in FIG. 3A. A fiberglass fabric may be selected as the mesh material because it is a strong, flexible, and hydrophilic material that allows nutrients to be replenished and simultaneously contain the microalgae inside the vessel. The fiberglass composite buoyancy control base can have two internal compartments. The upper compartment can be used to blow carbon dioxide from the base. The lower compartment can be filled with seawater during the growth phase to maximize surface area in which nutrients can diffuse across. The lower compartment can be filled with air during the harvesting phase to concentrate the algae by decreasing the IFV's volume prior to processing and/or harvesting the marine algae.

The vessel can include an electromagnetic core designed to retain the iron additions to the IFV, as shown in FIG. 3C. The electromagnetic coil in the $1^{st}$ generation 2 L prototype consisted of two wires wrapped around an iron core with opposite polarities. A timing circuit can allow the current to alternate between the two wires, thus changing the direction of the magnetic field. The wave function in the magnetic field causes the iron to oscillate between the two ends of the solenoid allowing it to mix with the aqueous media and algae inside the vessel.

The electromagnetic field strength is approximated by Ampere's Law as $B=\mu_o \eta I$, where $\mu_o$ is the permeability of the core, 11 is the number of turns per unit length, and I is the current. The B field strength is directly proportional to the current. The current can be regulated by changing the resistance in the circuit. Once the magnetic field has been induced, its magnitude is determined by a calibrated Hall Effect sensor. The magnetic field exerting at least 6.4 mT can retain reduced iron inside the vessel 6.4 mT, as shown in FIG. 3C.

Figure 5:
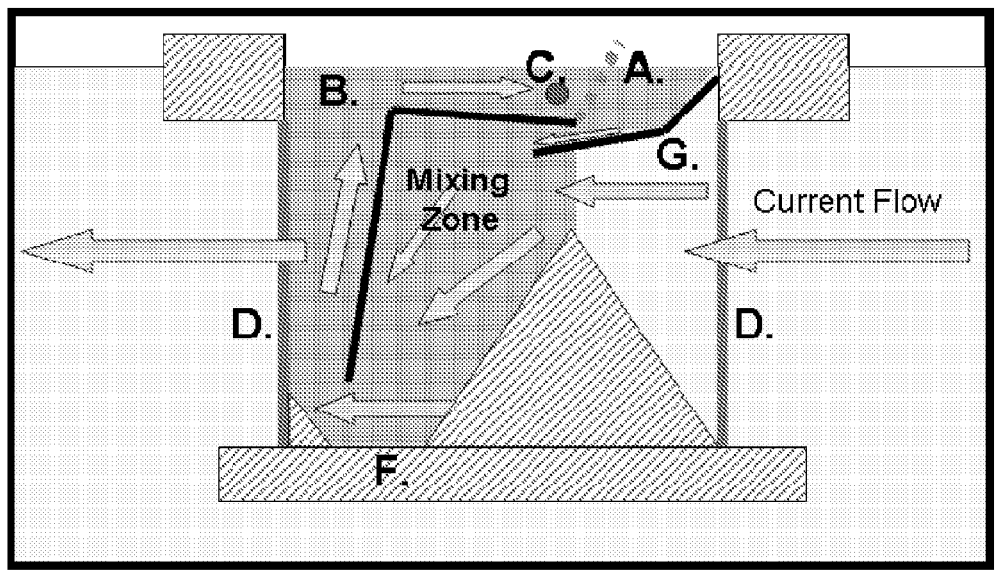
FIG. 5 shows a vessel design incorporating baffles to circulate the microalgae through the vessel.

The invention also provides for designs that can be utilized to streamline the vessel's functionality and operation by increasing circulation and/or mixing within a vessel, as shown in FIG. 5. For example, the vessel can be designed to mimic fresh water raceway pond functionality but in a vertical fashion. Increased circulation can allow for better mixing of nutrients and allow for desired or selected exposure of the microalgae to sunlight. The mixing and flow dynamics can be controlled by the design of the vessel dimensions and shape. Baffles within the vessel can be used to control fluid velocity and volumetric flow rates for liquid flowing in a recirculating pattern within the vessel and for liquids flowing through the vessel. The current in the surrounding environment can also be utilized to prevent fouling of the mesh materials by directed current flow across the mesh material or by powering a mechanical cleaning device. In some embodiments, the current can be used to generate power, which can be utilized by the vessel itself in any form, or by the processing platform.

To afford protection from the elements, the vessel, including the semi-permeable walls, can be rigid. In some embodiments of the invention, one wall can be rigid and the other can be flexible. The vessel can be designed to be resistant to damage by weather, current, or any large objects in the surrounding environment. The vessel can be designed to be rigid and protective, while not substantially restricting flow into and out of the vessel from the surrounding environment. In some embodiments, the vessel can be buoyancy controlled to allow the vessel to be submersed during inclement weather. Buoyancy control can be achieved by the top portion, the base, or any combination thereof.

Loss of microorganism and other nutrients through the upstream or current-facing side of the vessel is less of a concern than loss through the down-stream facing portion. In some embodiments, the up stream or current-facing side of the vessel can have a first pore size and the down-stream facing side portion can have pores of a second size that are smaller than the first size.

As shown in FIG. 5, a permanent magnet that spans the width of the vessel may be incorporated to increase the retentions time that the reduced iron sulfate (C) remains in the upper region of the vessel. The magnet can have a minimum field strength of 6.4 mT. In addition to a component for retaining iron, the vessel may also include components for retaining other nutrients. For example, the vessel may include mechanisms to concentrate nitrates and/or phosphates. The mechanism may include chromatography components, ion-exchange based materials, e.g., ion-exchange columns, and/or affinity based materials, e.g., affinity columns. Any of the vessels described herein may have components for concentration and/or retention of one or more nutrients, e.g., iron, nitrate, and/or phosphate compounds.

Stainless steel sieved gate (shown as dashed lines between C and A in FIG. 5) with a pore size less than the organism. In some embodiments, the gate is enclosed by the vessel. For example, the gate may be entirely enclosed by the vessel, or at least partially enclosed by the vessel. The gate may be movable between a blocking position and an open position. The gate may be lifted or moved out of a blocking position to an open position to allow the organism to circulate. The gate may be lowered or put in a blocking position to concentrate and harvest the organism (A). FIG. 5 shows the gate (dashed line) in a blocking position.

FIG. 5 indicates a deficient nutrient feed point (B). Feeds that are low in concentration in the surrounding environment can be added at point B. The deficient nutrients that can be fed to the vessel include any nutrient discussed herein. In some embodiments, the nutrients include iron, phosphate, and/or nitrate compounds. The iron can be fed as an iron compound, such as iron sulfate, or iron can be fed to the vessel as part of a biodegradable polymer or material that releases iron over time, as discussed herein. The biodegradable polymer or material can also include other nutrients, such as nitrate compounds and/or phosphate compounds. Nitrates can also be fed in the form of ammonium, ammonium ferrous(II) sulfate (magnetic), or ammonium bicarbonate. Nitrates and other nutrients can also be sourced from waste water, secondary waste water, run off, chicken feed, agricultural waste, or any low-cost nutrient source and then fed to the vessel. The nutrient feed can be controlled automatically or manually. The nutrient feeding may be controlled based on the concentration of the nutrient in the vessel, the growth rate and/or the concentration of the organism. A nutrient feeding component for feeding one or more nutrients can be included in any of the vessels described herein.

Uses the current's kinetic energy to thoroughly mix the micronutrients and the microalgae. The mixing of nutrients and algae can be achieved by baffles within the vessel that direct the fluid in a recirculating pattern. The vessel may be positioned within a flowing current. In FIG. 5, current flows into the vessel at the right-hand side (D right) and exits the vessel at the left-hand side (D left). The movement from right to left forces circulation within the vessel in the direction indicated by the arrows, which forms a recirculating pattern. The circulation can be created by a Venturi effect caused by the flux of fluid through the reactor from the upstream portion of the vessel to the downstream portion of the vessel. The amount of current flow used for circulation can be selected in a variety of manners, e.g., by altering the exposed surface area on the right hand side of the vessel and/or the surface area on the left-hand side D. In this configuration, the vessel has an upstream, or current-facing side and a downstream or a side that is not facing the current. If the current of the surrounding environment is fixed, the vessel may be fixed in a proper orientation. If the current is not fixed, then the directionality of the vessel may be controlled based on the current's direction. The control of the vessel's orientation can be automatic or manual.

As described above, orientation of the vessel relative to the current in the surrounding environment can plan an important factor in determining the circulation rate within the vessel. To account for this, the vessel can be designed such that the orientation of the vessel with respect to the direction of current flow can be controlled. A self-orienting mechanism capable of orienting the direction of the vessel can be provided. Mechanical features, such as vane-like features, can be used to self-correct or self-orient the direction of the vessel such that a desired flow of water through the vessel is achieved. For example, one or more fin, protrusion, channel, flap, or shaped feature can be provided for the vessel. A self-orienting mechanism can be provided in a stationary position relative to the vessel, or can be movable relative to the vessel.

In some embodiments, the vessel orientation with respect to the current is such that maximal flow through the vessel is achieved. In other embodiments, the vessel orientation can be such that flow through the vessel is lower than the maximal flow through the vessel. For example, if maximal flow is achieved by placing the incoming mesh side the vessel perpendicular to the flow, a lesser amount of flow can be achieved by placing the incoming mesh side at an orientation that is not perpendicular to current flow in the surrounding environment.

Uses the current's kinetic energy to concentrate the microalgae. Once the sieve gate shown in FIG. 5 is placed in a blocking position, the circulation, as described above, can be utilized to concentrate the microalgae against the sieve gate.

All the microalgae spend the same cumulative time in the sun exposure zone (between A and B in FIG. 5). The amount of time spent exposed to the sun can be controlled based on the circulation rate through the vessel and the cross-sectional area of the channels that allow exposure to the sun relative to the cross-sectional area of the other channels in the vessel.

The recirculation caused by the flux of water through the vessel maintains a constant microalgae density throughout the circulating/recirculating portion of the vessel.

The vessel shown in FIG. 5 can be designed for high Reynolds and Péclet number to insure it is in the convection regime for consistent nutrient and organism density.

The pivot point (G) shown in FIG. 5 can control the incoming water velocity. As described above, circulation may be controlled by a variety of manners. Here, an incoming water gate can control or restrict the rate of water entering the vessel.

If necessary, the vessel percolates or sparges carbon dioxide from the base (F) shown in FIG. 5 in an effort to achieve higher microalgae densities.

A hydrophilic, charged, porous material (D) shown in FIG. 5 can allow environmental micronutrients and waste organic acids to cross freely but contain the microalgae. This can be achieved by selecting an appropriate pore size, e.g., less than about 5, 10, 15, 20, 30, 50, 100, or 150 μm pore size (or any other pore size described herein).

Organisms and Metabolic Engineering

While microalgae and plankton have been referred to as organisms to be grown within the vessels, a variety of organisms can be grown in the vessels described herein. These organisms can include plankton, diatoms, algae, phytoplankton, and zoo plankton. The organisms to be grown can be selected based on geographic considerations. The organism can be any autotrophic or photoautotrophic organism. In some embodiments, the organisms grown within the vessels are more than one type of organism. For example, symbiotic organisms can be grown in conjunction with each other, or one organism may be grown during a first phase and a second organism may be grown during a second phase. In some embodiments, the organisms grown in the vessel can include an organism that performs nitrogen fixation. Nitrogen-fixing organisms can be grown with algae or any other organism in a symbiotic relationship. Examples of organisms that perform nitrogen fixation include *Richella intracellularis*, nitrogen-fixing blue-green algae, nitrogen-fixing cyanobacteria, and *Trichodesmium*.

The organisms, e.g., microalgae, utilized herein can be metabolically engineered for the efficient conversion of the nutrients to further increase the microalgae growth rate, improve product yields, decrease vessel requirements, and maximize the overall system productivity. The microalgae can be engineered to: increase fatty acid content and renewable fuels, e.g., biodiesel, productivity, manufacture industrial enzymes, synthesize personal care/medicinal proteins, and/or manufacture specialized fuels, e.g., jet fuel.

Isolate Local Wild Type Strains and Seed Culture Growth

In some embodiments, a large microalgae seed culture can be inoculated at the time the iron is added to the vessel to accelerate microalgae growth relative to diatoms. Microalgae can be the dominant species grown and harvested due to its higher initial concentration. Local wild type strains, which may be preferred, can be used such that new species are not introduced into the local environment. Local microalgae and diatom strains can be characterized for specific growth and nutrient requirements. As well, environmental parameters can be determined such that microalgae or diatom growth can be selectively induced.

Processing Platform

The vessel products (e.g., biomass produced by growth of or production by organisms grown within the vessels) can be harvested using a processing platform 1010 (see FIG. 10B). The processing platform can be a mobile unit that can be connected to the vessels 1012 described herein. The processing platform may be in fluid communication with an interior region of one or more vessel. In some embodiments, the processing platform can be connected to the vessels via a connector 104. In some embodiments, a connector may be a hose, pipe, or channel. In some embodiments, the processing platform and/or vessels can include a pump, a positive pressure source, or a negative pressure source, to transfer organisms within the vessel to and/or from the processing platform. The processing platform can optionally connect to each vessel directly. Alternatively, the processing platform can connect to one or more hubs, which can connect to one or more vessel. A processing platform can be connected to any number of vessels, including but not limited to one or more, two or more, three or more, four or more, five or more, six or more, seven or more, eight or more, nine or more, ten or more, twelve or more, fifteen or more, twenty or more, thirty or more, forty or more, or fifty or more vessels.

The processing platform can be located on a rig or an oil tanker. The processing platform can be located on a buoyant or floating support. The processing platform can also be located on land, which may be in close proximity to a body of water. For example, the processing platform can be located on a shoreline.

The processing platform can process organisms in real-time, after a certain period of time, or periodically. Lipids contained within organisms can be recovered and processed into biodiesel. Carbohydrates and proteins contained within the organisms can be collected and used in products for human or animal consumption. Seawater can be rejected and returned to the ocean. The processing platform can produce substantially no toxic or hazardous waste streams.

Methods

Microalgae Physiology:

The target culture density can be controlled. In some embodiments, the target control density is in the range of about 1 µg/L to 100 g/L, 100 µg/L to 50 g/L, or 1 to 10 g/L.

Nutrient uptake rates can be measured and accounted for to sustain selected growth rates or biomass production rates.

The waste organic acid accumulation rate can be measured and accounted for. The rate of waste organic acids transport out of the vessel through the permeable mesh membrane may also be controlled by adjusting the circulation rate, or by selecting preferred mesh materials.

The iron concentration can be measured and controlled. Iron concentration may be a limiting factor for growth or may provide a means to control growth rate.

The concentration of silica, nitrogen, phosphorous, and carbon nutrients can also be measured and controlled. In some embodiments, these nutrients can pass through the membrane at a higher rate than iron and biomass. The concentration of silica, nitrogen, phosphorous, and carbon nutrients can affect growth and productivity of the microalgae and a lower non-inhibitory concentration for these compounds can be determined.

The iron feed profile can be selected for a number of parameters. The iron feed profile can be adjusted based on the growth of the organism within the vessel, or the iron feed profile can be adjusted to maintain constant or varying iron concentration.

In some embodiments, various strains may have different specificity for different iron compounds. The iron compound used can be selected for efficient growth of the organism of choice of vice-versa, the organism can be selected for efficient growth using a predetermined iron compound.

The production of renewable fuel and protein yield per gram iron can be measured and optimized based on other parameters described herein.

Various environmental parameters that naturally select for and maximize specific growth rate can be monitored and accounted for.

Iron Fertilization Vessel

Iron containment and the concentration of iron within the vessel may be measured using optical density or chelating/pH measurements on samples taken inside and outside the vessel.

Microalgae containment may be measured using optical density measurements from samples taken inside and outside the vessel during growth experiments.

Membrane material investigation can be selected such that it is durable and hydrophilic.

Vessel Automation, Sampling and Processing

In some embodiments, LCMS can be used to measure water samples upstream and downstream of the vessels. Other parameters that can be measured include optical density (to determine the concentration of the culture), iron concentration in the culture, and culture pH. These procedures, including sampling and processing of the biomass using the methods described herein, can be automated.

Organism Selection and Preparation

The following provides one example of organism selection and preparation. First, local sea water can be retrieved, which may include seawater from the Sea Cliff Beach Pier in the Monterey Bay, to be used as a first source of seawater. Low silicate sea water can be used as a second source of seawater. Iron may be added to each sea water type to bring its iron concentration to 5 nM. 1 mM sodium bicarbonate can be added to each sea water type as a substitute for $CO_2$ gas. Both sea water stocks can be filtered with a 0.2 µm hydrophilic membrane. 15 g agar can be added to 500 mL of each sea water stock. The agar may be dissolved by microwaving until everything it is melted. The sea water stocks can be removed from the microwave and shaken. The petri dishes can be filled to about half full. The petri dishes can be let to solidify and stored upside down in a cold room.

Next, unfiltered local marine water can be streaked on both plate types. They may be incubated on the bench in the presence of a constant full spectrum light source. From the filtered local marine water plates, an isolated diatom colony may be picked and streaked on new local marine water plates. From the low silicate plates, an isolated microalgae colony may be picked and streaked new low silicate plates. These plates may be incubated until single colonies grow. A single diatom or microalgae colony can be picked from a plate and a sterile test tube filled with 5 ml of filtered local marine water stock and with 5 nM Fe and 1 mM $NaHCO_3$ (Solution C) can be inoculated. This may be incubated in a shaker with a full spectrum light source present until the culture reach 1 OD at 600 nm. Next, a sterile 500 mL flask filled with 50 mL of Solution C and all 5 mL of the first generation seed culture can be inoculated. This can be incubated in a shaker in the presence of a full spectrum light source present until it reaches 1 OD at 600 nm. The secondary seed culture should either be (i) used to inoculate a closed water time-course experiment and/or (ii) split into a master stock for each specimen.

Electromagnetic Intensity

The minimum electromagnetic field required to bind the bulk of the trace metals can be determined. In a clear fresh water tank with constant agitation, the electromagnetic potential can be maximized to bind all the trace metals to the sealed coil. Starting from the maximum potential, the electromagnetic potential may be incrementally decreased until trace metals start to release from the coil allows for the determination of the minimum electromagnetic field required to bind the trace metals. After each field adjustment, a spectrophotometer measurement at 595 nm can be taken. This can continue until the spectrophotometer readings increase 10% over or under the baseline.

Iron Compound Selection

Introducing iron into an ocean environment typically induces the largest biological response of all the trace metals. Iron sulfate has been the substrate used in most open water fertilization experiments. However, it may not be the best choice because it induces the growth of both plankton and diatoms. Based on the multiple composition profiles in the literature, plankton is preferred over diatoms because it has a significantly larger lipid and protein composition. The diatom composition is skewed towards ash/fertilizer products. Therefore, an iron compound that is preferentially selected by plankton may be preferred.

A selected iron compound can be chosen by performing laboratory growth time course experiments using different iron compounds and 0.2 µm filtered seawater. The idea is to maximize plankton specific growth while minimizing the diatoms' at the same time. Also fed-batch introduction of the iron compound may promote plankton growth over diatoms.

Iron compounds can be selected for specificity for diatoms and microalgae. As well, the amount of iron can be selected such that a minimal amount of iron is used to maintain a desired growth rate. Iron concentrations can be about or up to about, or at least about 5.00, 2.50, 1.25, 0.63, 0.31, 0.16, 0.08, 0.04, 0.02, 0.01, or 0.005 nM iron.

In some embodiments of the invention, the iron compound is formed within a biodegradable material. The biodegradable material can be any suitable polymer that allows for desired release of iron compound at the proper concentration. The biodegradable material can allow for time-release of the iron compound and can also allow for the iron compound to be encapsulated within a large particle that will not pass through the semi-permeable walls of the vessel. Furthermore, encapsulation of the iron compound can reduce or prevent oxidation of the iron compound. Oxidation of the iron compound can change the magnetic properties of the iron.

The following is an exemplary procedure to test for desired iron concentration:

First, make a stock local sea water solution with 1 mM sodium bicarbonate (Solution A), a carbon source substitute for the $CO_2$ gas. Add iron sulfate to 250 mL of the Solution A to achieve a concentration of 5 nM (Solution B). Achieve the above growth media iron concentrations by serially diluting Solution A with Solution B. Add iron contain solutions to test tubes and inoculate with the appropriate strains. Incubate the test tubes in the presence of a continuous full spectrum light source. From the above experiment, the highest iron concentration level that will induce microalgae and impede diatom exponential growth (lowest concentration level diatoms) can be determined.

Maximize Microalgae/Plankton Specific Growth Rate

Iron is one of the first limiting compounds in ocean environments (See, e.g., Scharek R, Van Leeuwe M A, De Baar H J W (1997). "Responses of Southern Ocean Phytoplankton To The Addition Of Trace Metals" Deep-Sea Research II Vol. 44 (1-2): 209-227). Once iron is supplemented, the next limiting trace metal or nutrient can be identified. Utilizing microbial physiology, plankton specific growth rate can be maximized by supplementing quickly depleted nutrients and/or trace metals to the vessel. In essence, the vessel can be used as an open-water fermenter to achieve high growth rates and plankton density. After maximizing growth by regulating extracellular factors, the plankton can be metabolically engineered for the efficient conversion of the nutrients to further increase the plankton growth rate, improve product yields, decrease vessel requirements, and maximize the overall system productivity.

Time-courses can be conducted to track the depletion rates of important nutrients and trace metals by microalgae, diatoms and other organisms. Depleted nutrients can be fed at a rate that sufficiently alleviates the observed rate-limiting factor that occurs during the exponential growth phase. At that point, a new rate limiting compound can be identified and fed accordingly. This process of identifying and feeding deficient nutrient can repeat itself until the predetermined growth rate is achieved or all the environmental parameter modification options have been exhausted.

In a 20-55 L closed water environment, add filter sterilized local sea water with 1 mM sodium bicarbonate or blow carbon dioxide from the base of the 2 L prototype as shown in FIG. 9. At time zero, inoculate the vessel interior with the 50 mL seed culture and start feeding iron and other depleted nutrients. The feed rate of the iron and depleted nutrients will be ramped up according to their utilization profile from previous experiments and the current instantaneous growth rate. Take samples at 2 hr intervals until the culture reaches the stationary phase. At each sampling point measure the pH, the optical density at 600 nm, and the mass density inside and outside the vessel. Analyze the samples for micronutrient concentrations and their depletion rates, especially phosphates, nitrates and bicarbonates. Analyzing for nitrates can give some insight in to whether this concept can effectively be used to remove excess nitrates that have a hand in inducing Harmful Algae Blooms (HABs). Analyzing Bicarbonate concentrations may give some insight as to how large a role this concept may play in recycling greenhouse gases and global warming With total microalgae amounts, how much carbon dioxide and nitrates are being removed from the environment and converted to microalgae that will be processed into renewable fuels, protein extract, and glycerol can be determined.

Additional Technologies

In conjunction with the systems, methods, and devices described herein, techniques and scientific knowledge from the following areas can also be harnessed:
1. Fatty acid extraction and transesterification
2. Glycerol purification and recovery to sell to pharmaceutical and personal care product manufacturers.
3. Bulk protein, amino acids, and carbohydrate recovery and packaging.

Microalgae Bioprocessing

Figure 8:
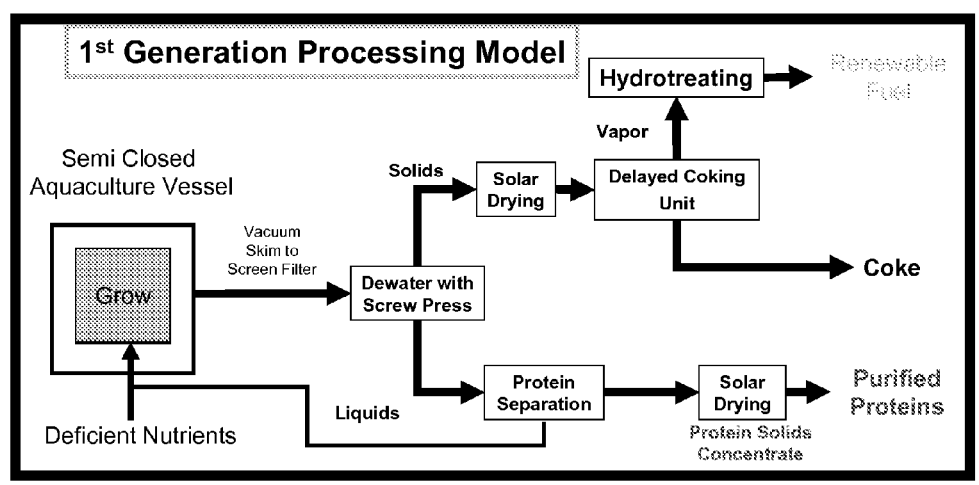
FIG. 8 is a diagram depicting microalgae processing into hydrocarbon fuels and purified proteins.

One example of a conversion process from microalgae growth to the renewable fuel and protein products, described herein, is shown in FIG. 8. The biomass grown in the vessels described herein are initially screen filtered prior to dewatering with a screw press. The microalgae oils are dried prior to being fed to the delayed coking unit and then hydrotreated. During the early implementation of this process, the extracted microalgae oil can be sold to fossil fuel refiners to be coprocessed with their incoming crude oil.

During an implementation, the biomass from the vessels may be screen filtered and then dewatered with a screw press. The dried biomass may undergo protein separation. Then solar drying may occur to for purified proteins.

Delayed Coking

Delayed coking is a thermal process which has two major reactions—thermal cracking and polymerization. Thermal cracking is the mechanism through which molecules of high molecular weight in the feed stock are decomposed into smaller, lighter molecules that are fractionated into their end products. Polymerization is a reaction through which many small hydrocarbon molecules are combined to form a single large "coke" molecule of high molecular weight. A typical coke has 100 to 200 carbon molecules.

The main objective of the delayed coking unit is to convert microalgae oil to lighter products of higher value and to produce a coke product. In some embodiments, fresh microalgae feed is preheated through a heat exchange system prior to entering the bottom of the coker fractionating tower. The fresh microalgae feed is mixed with recycle from the unit before being pumped through two fired heaters. The effluent from the heaters then enters the bottom of the coking drums where the gaseous products pass out the top and the liquid soaks in the drum until it cracks into lighter products that will exit the top of the drum or forms coke. The liquid and gaseous products resulting from the thermal cracking are separated into the desired products by fractionation in a distillation tower before being deoxygenated via hydrotreating. The coke product in the coke drum is removed batchwise from the drums after cooling.

Hydrotreating

Conventional hydrotreating technology of microalgae oil extract produces a high quality product that is compatible with existing fuel infrastructure. Hydrotreating deoxygenates microalgae feedstock by adding hydrogen to produce a highly-stable renewable diesel fuel with a higher cetane value, lower cloud point and lower emissions than biodiesel and traditional petrodiesel.

Facilities/Location

The vessels can be implemented at sites that are near seawater, rivers, estuaries, oceans, lakes, or any body of water. In some embodiments, the site is near rail service to facilitate transportation of goods.

The growth parameters can be optimized and the microalgae's metabolic pathways can be engineered to achieve a significantly higher specific growth rate. Increases in the microalgae's specific growth rate, the initial culture density ($P_i$) and final culture density ($P_f$) can increase the overall system productivity and lower the total vessel requirement.

As shown in FIG. 11, a final microalgae concentration can be at least about, up to about, or about 25 g/L, thus requiring only 16 vessels to produce 5M gallons of fuel per year. Sixteen vessels can utilize or require only 1.25 acres of ocean surface area.

Advantages

The invention provides for a systems, devices, and methods that allow for the growth, concentration, and harvesting of mass marine biomass induced by iron fertilization for commercial biofuel, e.g., biodiesel, production. The benefits of ocean and open-water farming are numerous and far outweigh any benefits of any land based algae efforts.

The devices and methods describe herein have comparatively low feedstock production costs. The reduced production and distribution costs are largely due to the following advantages: (i) very little overhead is required to run and maintain farms in the open ocean, (ii) production vessels can be quickly fabricated and deployed off any coast, close to end users particularly in major urban areas and near transit arteries with very little initial capital, (iii) the ocean has a free and abundant supply of all the required nutrients to produce renewable fuels, except the very inexpensive iron compounds, (iv) feedstock production is highly scalable, and (v) virtually no waste streams are generated, which would require additional disposal costs and fees.

Capital and Operational Costs

The systems described herein have a number of advantages. The vessel construction is extremely low compared to bioreactors. The vessels are modular and portable. The vessels do not require highly skilled labor to operate and optimize it like bioreactors. As a result, they can be established in most coastal regions of the world; moreover, they do not require laborers with specialized skills.

The vessels do not utilize limited resources like land and fresh water. It reduces rents/mortgages requirements due to the minimum land use. The cultivation, harvesting, and microalgae fuel processing stages can be done at sea thus eliminating the cost of leasing land. Most land requirements can be for storage and management office space. The invention does not compete with other developed land uses such as farming for food or residential/commercial developments. In fact, the only resource that is required is the widely abundant iron. This minimizes or reduces chemical purchasing requirements to iron and downstream processing chemicals such as ethanol/methanol and base catalyst. The majority of the cultivation nutrients are provided and continuously replenished by the ocean for free, thus lowering the raw material expenses.

The magnetic iron retention and/or mixing mechanism increase the overall yield and productivity of the system thus minimizing the vessel requirements and capital investment. The ocean provides the kinetic energy required to keep the system well mixed for free thus further reducing energy costs and requirements.

Additionally, no waste streams are produced. There are no waste streams because (1) the supernatant is returned to the ocean (during growth and during dewatering/harvesting), (2) the biomass lipids are converted to biodiesel, (3) and the carbohydrate/protein extract are packaged for human/animal consumption.

The use of buoyancy as the concentrating mechanism to reduce vessel volume prior to processing in order to minimize the volume that needs to be pumped and centrifuged provides a significant advantage. Using buoyancy is a less energy intensive method other mechanical methods.

In comparison to open-ocean iron fertilization where biomass grown is not harvested, the invention provides for product revenue streams that are generated from (1) converting the microalgae lipids to renewable fuels, and (2) extracting the algal carbohydrate/protein for human/animal consumption.

Also, tax credits from both carbon sequestration and biodiesel/renewable fuel production can be obtained.

Manufacturing Benefit

In addition to the cost benefits, there are several manufacturing benefits to take into account. The system that we described above is constructed of modular components that can be easily fabricated out of composite materials, e.g., fiberglass or carbon fiber composite materials, once the molds for the parts have been made. Because of the modular composite components, these vessels can easily be repaired, replaced, and relocated. When the vessel is displaced by a storm, they can easily be located if the system components are both filled with air making them buoyant and a locating beacon is installed. Finally, the system is scalable to sizes that are impractical on land due to a variety of reasons, including volume and surface area limitations.

Economic

The invention provides for system, devices, and methods that can create a domestic and worldwide renewable hydrocarbon fuel source, create worldwide distribution, bioprocessing, manufacturing, and engineering jobs, and can potentially replace the need for all imported diesel fuel products. Also, it ensures the US maintains a technological advantage in developing and deploying energy technologies.

Engineering

The invention provides for a platform technology that can be used for generating medicinal, industrial, and nutritional proteins worldwide.

Military

The invention allows for local fuel production and depots around the world. This can be useful to military installations that are dispersed throughout the world, but have access to aqueous environments.

Environmental and Safety Issues

The environmental benefits are straight forward but just as important as the other benefits. The biomass produced fixes dissolved $CO_2$, causing surrounding atmospheric $CO_2$ pressure to decrease. The ocean waters are also simultaneously deacidified. The oceans can be deacidified by fixation of dissolved carbonate and bicarbonate The invention can be used to restore coastal ecosystems through bioremediation. The invention can be used to remediate coastal estuaries and river deltas by reducing nitrogen and phosphorous concentrations and eliminating unwanted hazardous algae blooms.

Another benefit worth discussing is the ramification and cleanup of an accidental spill of biodiesel or unprocessed marine biomass. Since the biomass/biodiesel is biodegradable, it can be either consumed or degraded by other organisms in an ocean environment over the course of no more than 17 days.

In some instances, the organisms to be grown can be contained within the vessels. This can reduce the environmental impact of organisms on the surrounding environment. For example, genetically modified organisms can be substantially contained within the vessel.

The devices and methods herein can be designed such that compliance with EPA, NEPA, and London Protocol regulations is met. In the open ocean, time courses experiments can be conducted to determine if there is any perturbation to the surrounding marine ecology and how fast the surrounding marine environment recovers after cultivating and harvesting large quantities of plankton. The invention provides for systems, devices, and methods that allow for farming of the oceans without disrupting ecological systems and continue to comply with NEPA and the London Protocol.

Another potential environmental and safety concern is what effect does creating an artificial magnetic field has on the surrounding ecological system. Electromagnetic field intensity can be controlled such that the ocean habitat's health and the safety of the employees is protected.

Because the plants can be located throughout the world, this can minimize the fuel consumed while distributing fuels to end users.

With all these benefits, the cost and energy balance equations are very much in favor of our system.

Quantitative Impact: Scaling Calculation

The following calculations were made to determine the number of vessels and ocean surface area required to replace the US daily consumption of petroleum distillate. First, the time needed for a culture to start at an initial concentration, $P_i$ and grow to a final extended vessel concentration, $P_f$, needs to be calculated from Equation 1, shown in FIG. 13. Once the time is calculated the biomass and lipid production rates per vessel can be determined from equations 2 and 3 shown in FIG. 13, respectively.

Since glycerol is replaced by methanol or ethanol during the triglyceride transesterification, we assumed that the lipid content weight is approximately equal to the biodiesel product weight. As a result, the biodiesel production rate per vessel is approximated by equation 4 shown in FIG. 13.

Now that the biodiesel production rate per vessel has been approximated, we can determine the ocean farm size required to displace the petroleum distillates used by the United States each day by equations 5 and 6 shown in FIG. 13.

The results of the above calculations based on literature values for the growth rate are listed in the table shown in FIG. 14. In order to greatly reduce the vessel requirement numbers in FIG. 14, we can engineer the vessel and the stains to achieve a significantly higher specific growth rate, initial culture density ($P_i$) and final culture density ($P_f$). Improving the above three factors can increase the overall system productivity and lower the total vessel requirement. At the very least, we believe that this system can replace 25% of the petroleum fuel consumption in the United States.

Application: Renewable Fuel and Protein Synthesis

Figure 6:
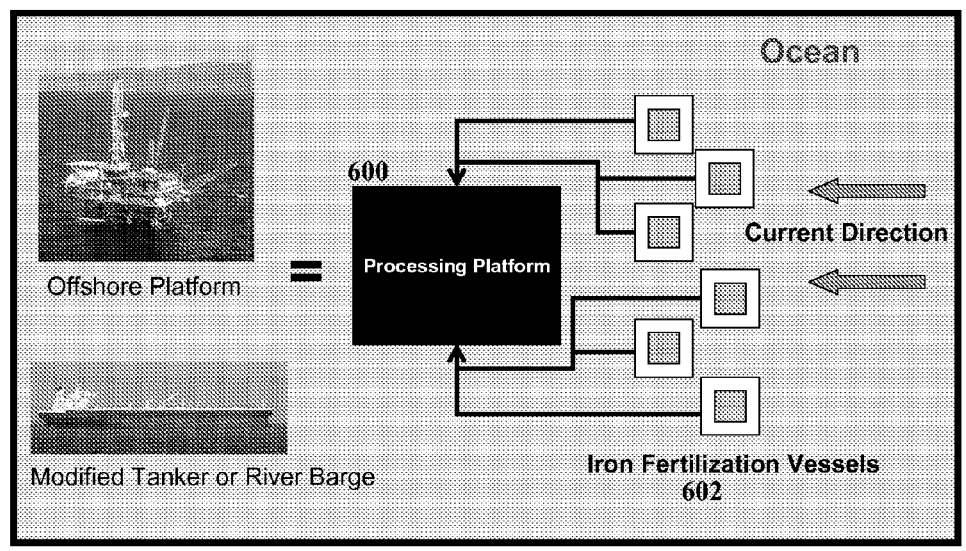
FIG. 6 shows an offshore aquaculture implementation to generate renewable hydrocarbon fuels and proteins.

In some embodiments of the invention, the vessels are located around oil drilling platforms off the US Pacific and Gulf of Mexico coastlines. Offshore drilling platforms have been in the service of the oil industry for decades. Once the oil reserves are depleted, these platforms are capped and left to decay into man-made reefs. These inactive offshore platforms dot the Gulf of Mexico coastline without a useful purpose until now. Offshore platforms are ideal for mooring aquacultures. FIG. 6 displays a possible layout around an out of service drilling platform 600. The platform offers a place to harvest and process the microalgae on site into renewable hydrocarbon fuels, protein supplements, and glycerol which is preferred because it is more efficient to transport liquid fuels. As shown in FIG. 6, a tanker or river barge retrofitted with the tools necessary for doing the microalgae to renewable fuels conversion at sea is also a viable option.

In some embodiments, one or more vessel 602 may be provided upstream of the platform 600.

Application: Bioremediation of Coastal Estuaries and River Deltas

Figure 7:
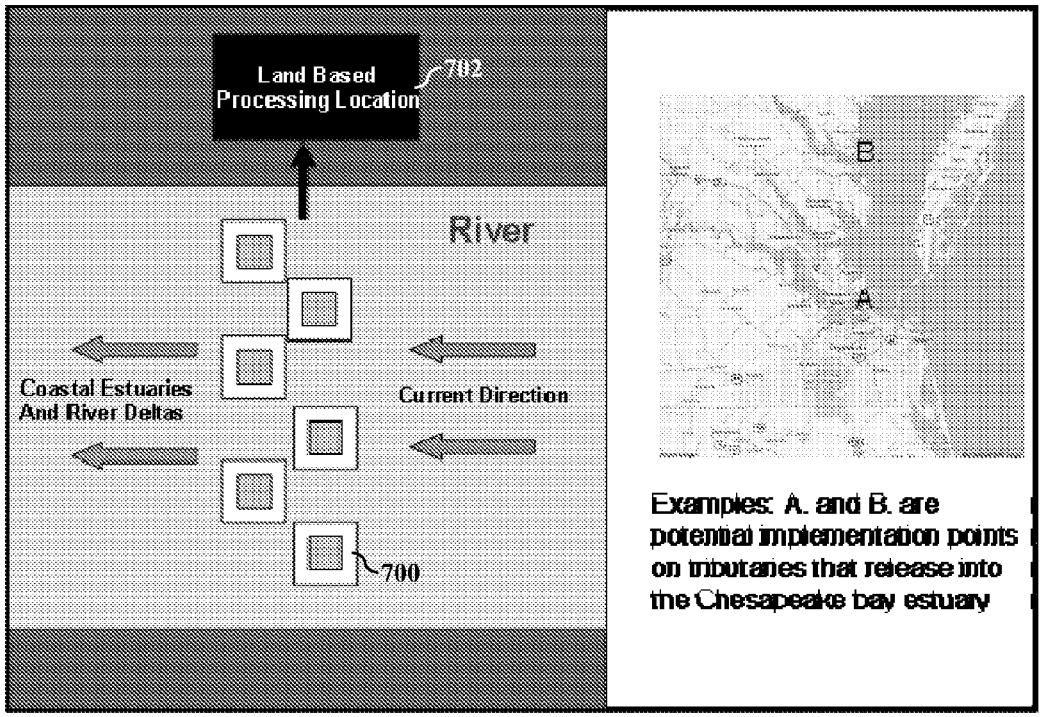
FIG. 7 shows an implementation of vessels for nitrogen and phosphorous micronutrient bioremediation along rivers and tributaries prior to reaching coastal estuaries and deltas.

The devices and methods described herein can be used for remediating coastal estuaries and river delta regions, as shown in FIG. 7. The right-hand side of FIG. 7 shows two potential implementation points on tributaries that release into the Chesapeake Bay estuary. As an example, the vessels 700 can be implemented for nitrogen and phosphorous micronutrient bioremediation along rivers and tributaries prior to reaching coastal estuaries and river deltas. Microalgae grown in vessels described herein can be processed into purified proteins and hydrocarbon fuels that may be packaged and sold in the local markets. There may be fewer policy hurdles to cross to clean up coastal dead zones and an opportunity to build a positive reputation with the United States government and the American people.

Along the coast and tributaries, iron is usually not the limiting nutrient. Once the deficient nutrients for microalgae growth are identified, they can be fed into the vessel in quantities that correlate to the biomass density. The rate at which nutrients are fed into the vessel may be proportional to the uptake rate determined in a laboratory closed water time course experiment. Controlling the harvest rate may directly affect the microalgae concentration and indirectly affect the nitrogen and phosphorous uptake rate. As described before, the harvested microalgae can be processed on site into renewable hydrocarbon fuels, concentrated proteins, and glycerol to be sold on the local markets. These alternative profit streams ensure that this remediation endeavor is economically viable. As shown in FIG. 7, the processing plant 702 can be located on land rather than on water because land is nearby.

Any components, configurations, characteristics, features, or steps as known in the art may be used in any of the embodiments discussed herein. See, e.g., Kalra, A. and W. S. LLP. (2006). "BiodieselTax Credits"; Walford, L. A. (1958). Living Resources of the Sea: Opportunities for Research and Expansion. New York, Ronald Press; and Löscher, B. M. (1999). "Relationships among Ni, Cu, Zn, and major nutrients in the Southern Ocean." Marine Chemistry 67: 67-102, which are hereby incorporated by reference in their entirety.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A vessel comprising:

a semi-permeable exterior wall, wherein the semi-permeable exterior wall selectively retains a microorganism over water-soluble nutrients;

a baffle for directing flow within the vessel in a recirculating pattern when fluid is passed through the vessel; and a self-orienting mechanism capable of orienting the direction of the vessel with respect to the direction of a current flow when the vessel is positioned in a current.

2. The vessel of claim 1, further comprising a magnet or electromagnet that is at least partially enclosed by the semi-permeable exterior wall.

3. The vessel of claim 2, wherein the magnet or electromagnet spans the vessel's width.

4. The vessel of claim 1, further comprising a sieved gate that is at least partially enclosed by the semi-permeable exterior wall, wherein the sieved gate is movable between a blocking position and an open position.

5. A vessel comprising:

a buoyant top;

a buoyancy-controlled base; and a semi-permeable mesh material connecting the buoyant top to the buoyancy-controlled base, wherein the semi-permeable mesh material selectively retains a microorganism over water-soluble nutrients.

6. The vessel of claim 5, further comprising a magnet or electromagnet.

7. The vessel of claim 6, wherein the magnet or electromagnet forms a coil.

8. The vessel of claim 5, wherein the semi-permeable mesh material is collapsible.

9. The vessel of claim 5, wherein the buoyancy-controlled base is movable with respect to the buoyant top.

10. The vessel of claim 9, wherein the buoyancy-controlled base includes one or more compartment that is capable of being filled with gas that causes the buoyancy-controlled base to rise.

11. The vessel of claim 9, further comprising one or more reinforcing beam that limits the mobility of the buoyancy-controlled base to a vertical direction.

12. The vessel of claim 1, wherein said vessel is configured for constant replenishment of said water-soluble nutrients.

13. The vessel of claim 1, wherein said vessel is configured for constant dilution of waste materials secreted by said microorganism.

14. The vessel of claim 1, wherein said vessel is configured to use the kinetic energy of said current flow for mixing of said water-soluble nutrients and said microorganism.

15. The vessel of claim 1, wherein said baffle is configured to direct said flow within said vessel in said recirculating pattern via a Venturi effect.

16. The vessel of claim 1, wherein said vessel is configured to use the kinetic energy of said current flow to concentrate said microorganism.

17. The vessel of claim 1, further comprising a gate that controls the flow of said fluid as said fluid enters said vessel.

18. The vessel of claim 1, wherein said vessel is configured such that, during fluid flow through said vessel, said fluid modulates the temperature of said microorganism.

19. The vessel of claim 2, wherein said electromagnet is configured to retain magnetic materials capable of inducing growth of said microorganism.

* * * * *